United States Patent [19]
Kenney

[11] 3,983,149
[45] Sept. 28, 1976

[54] AMMUNITION PRIMING MIXTURES AND METHOD OF FORMING SAME

[75] Inventor: Joseph F. Kenney, Bridgeport, Conn.

[73] Assignee: Remington Arms Company, Inc., Bridgeport, Conn.

[22] Filed: Apr. 29, 1975

[21] Appl. No.: 572,829

Related U.S. Application Data

[63] Continuation-in-part of Ser. No. 489,704, July 18, 1974, abandoned.

[52] U.S. Cl. ............................ 260/435 A; 149/24
[51] Int. Cl.² ..................... C07F 7/24; C06B 41/02
[58] Field of Search ................ 149/24; 260/435 A

[56] References Cited
UNITED STATES PATENTS

| | | | |
|---|---|---|---|
| 1,443,328 | 1/1923 | Herz | 149/24 |
| 1,999,728 | 4/1935 | Herz | 149/24 |
| 2,150,653 | 3/1939 | Franz | 260/435 A |
| 2,239,547 | 4/1941 | Brun | 149/24 |
| 2,295,104 | 9/1942 | Garfield | 149/24 |
| 2,589,703 | 3/1952 | Kenney | 149/24 |
| 2,702,745 | 2/1955 | Kenney | 149/24 |
| 3,002,012 | 9/1961 | Blackensto | 260/435 A |
| 3,301,882 | 1/1967 | Taylor | 260/435 A |
| 3,320,104 | 5/1967 | Stadler | 149/24 |

Primary Examiner—Samuel W. Engle
Assistant Examiner—Donald P. Walsh
Attorney, Agent, or Firm—John H. Lewis, Jr.; Nicholas Skovran; William L. Ericson

[57] ABSTRACT

Ammunition rim fire priming mixtures are commonly prepared by mixing normal lead styphnate, a sensitizer, such as tetracene, an oxygen donor such as lead nitrate, and a frictionator such as ground glass. This invention relates to such a mixture and to center fire priming mixtures which consist of lead styphnate, tetracene, inorganic fuels and barium nitrate and to a method of forming them and is characterized by the use of lead styphnate which is formed in situ by the reaction of a water wet mixture of styphnic acid and a lead compound such as lead oxide (litharge), lead hydroxide, basic lead carbonate, or lead carbonate. The lead styphnate which results from the practice of this method has been isolated and subjected to X-Ray diffraction analysis confirming that this is a novel form of lead styphnate and is indeed a new compound. Important advantages of this invention are reduced cost, improved safety since it is unnecessary to prepare, precipitate, or separately handle pure or relatively pure lead styphnate and because the wet mixtures are insensitive, and improved percussion sensitivity of the resulting mixtures when dried for use.

6 Claims, 1 Drawing Figure

TETRAGONAL UNIT CELL OF NEW FORM OF
LEAD STYPHNATE $a = 11.22 \text{ Å}$
$c = 7.19 \text{ Å}$
$a/c = 1.56$
$V = a^2c = 905 (\text{Å})^3 = 9.05 \times 10^{22} \text{cm}^3$
5 Pb-Styphnate Molecules per cell

TETRAGONAL UNIT CELL OF NEW FORM OF
LEAD STYPHNATE $a$ = 11.22 Å
$c$ = 7.19 Å
$a/c$ = 1.56
$V = a^2c = 905 (Å)^3 = 9.05 \times 10^{22} cm^3$
5 Pb – Styphnate Molecules per cell

AMMUNITION PRIMING MIXTURES AND METHOD OF FORMING SAME

This application is a continuation-in-part of my application Ser. No. 489,704, filed July 18, 1974, nonw abandoned which was intended to cover only the method phases of the invention defined herein.

BACKGROUND OF THE INVENTION

Normal lead styphnate (normal lead trinitroresorcinate) is a well known primary explosive which has been widely used for the manufacture of percussion primers for small arms ammunition and the like where it first came into use as a replacement for fulminate of mercury. Normal lead styphnate is a very powerful, percussion sensitive explosive which is also quite sensitive to static electricity. The danger of handling it in pure, or relatively pure form, is such that it is normally handled only in small quantities, kept wet, and in rubber containers or "boats". Even with these precautions it has been known to detonate as the result of the stimuli of shock, friction, static electricity, or exposure to sparks or flame.

The normal lead styphnate of this invention is prepared in situ in a wet mixture of styphnic acid (trinitroresorcine) and a lead compound such as lead oxide (litharge), lead hydroxide, basic lead carbonate, or lead carbonate. In the resulting wet mixture the lead styphnate does not show any undesirable sensitivity to initiation by shock, friction, or static electricity and such wet mixtures can be handled in normal primer charging operations with little or no risk of accidental explosion.

As set forth in Davis "The Chemistry of Powder and Explosives", Page 440, Vol. II (1943) John Wiley and Sons, Inc., lead styphnate is commonly prepared by adding a solution of magnesium styphnate at 70° C. to a well stirred solution of lead acetate at 70° C. A voluminous precipitate of the basic salt separates. The mixture is stirred for 10 or 15 minutes; then dilute nitric acid is added with stirring to convert the basic salt to the normal salt and the stirring is continued. while the temperature drops to about 30° C. The product, which consists of reddish-brown, short, rhombic crystals, is filtered off, washed with water, sieved through silk, and dried, In the processes of filtration and washing undesirable impurities tend to be eliminated.

Other methods of producing normal lead styphnate are described in the patents of Edmund Herz, such as, U.S. Pat. Nos. 1,443,328 and 1,999,728, the latter process having been used commercially by applicant's assignee for many years in the making of many millions of small arms primers. This latter method is characterized by the preparation of lead styphnate by the interaction of a concentrated solution of magnesium styphnate with a solution of lead nitrate in the presence of free styphnic acid.

The presence of free styphnic acid.

The patent of Garfield U.S. Pat. No. 2,295,104, describes still another process of producing normal lead styphnate as does the patent to Brun U.S. Pat. No. 2,239,547.

When the first attempts were made to produce lead styphnate in accordance with the present invention, commercial styphnic acid was used and the resulting mixtures were found to be so sticky that they clung to the charging equipment and were found to harden to an undesirable degree preventing charging when the wet mixtures were stored for such periods as overnight.

In the commercial manufacture of styphnic acid, resorcinol is first sulphonated with 90% sulphuric acid. After the sulphonation is complete, nitric acid is added, the material nitrated and the styphnic acid precipitated. Some investigators (Franz, Wilkinson and Ehrlich U.S. Pat. No. 2,150,653) feel that when styphnic acid is so manufactured on a commercial scale, small amounts of nitrous and nitric oxides are present during the sulphonation. This, they felt, produces a dark brown material which may include some or all of the nitro derivatives of resorufin, the nitro derivatives of indophenol and the nitro derivatives of resazurin.

I have also discovered that styphnic acid produced by one of the commercial processes contains a minor amount of sulphuric acid. When styphnic acid is dissolved in amyl alcohol and the amyl alcohol solution extracted with water several times, the water extracts may be bulked together, evaporated to one-half volume, chilled, and the precipitated crystals of styphnic acid removed by filtration. Suuccessive repetitions of this technique of evaporating the water extract, cooling it to precipitate any remaining styphnic acid, filtering out the crystals, etc., followed by evaporation as far as possible in a steam bath and by evaporation in a vacuum oven at 65° C. resulted in the concentration of a black oily residue. This oily residue was found to have as its principal ingredient sulphuric acid which was undoubtedly carried over from the sulphonation process. Other impurities are also present in the oily residue and are believed to consist of one or more of the impurities referred to in the aforementioned U.S. Pat. No. 2,150,653 or in a later patent to one of the same inventors U.S. Pat. No. 2,246,963.

As will be noted from these patents, it was theorized that the presence of these impurities was helpful in the manufacture of lead styphnate and if the styphnic acid was too pure it was the practice of these inventors to add one or more of such impurities or to modify the process to insure that they would be produced.

Certainly the presence of these impurities had no adverse effects in the formation of lead styphnate by the methods of the prior art for in the precipitation, filtering, washing and drying of the lead styphnate, the impurities or lead salts formed from reactions with such impurities, were readily separated from the dense crystalline normal lead styphnate.

However, in the practice of applicant's process, wherein the normal lead styphnate is precipitated in situ in a priming mixture, there is no opportunity to eliminate the impurities or any products resulting from a reaction with the impurities. Although the impurities do not interfere with the production of the lead styphnate, by remaining in the mixture they profoundly affect the resulting mixture and it may become so sticky that it adheres to tools and charging plates and hence cannot be charged into primers in the usual way and the mixtures may harden up so quickly that they cannot be stored for the required length of time or handled in the normal manner.

Accordingly, when referring to lead styphnate for use in my invention, I refer to a relatively pure styphnic acid in the form of dense crystals of reasonably uniform shape and size and of the light color associated with the pure product. The dark brownish commercial styphnic acid or any other form of styphnic acid containing significant amounts of impurities such as sulphuric acid, the nitro derivatives of resorufin, the nitro derivatives of indophenol and the nitro derivatives of resazurin should not be used.

As has been indicated, there are known prior art methods of producing styphnic acid of the desired purity and the usual commercial styphnic acid may be adequately purified by dissolution and re-crystallization. It has also been noted that with some of the forms of commercial styphnic acid the dry product may be selectively screened to eliminate irregular, large, agglomerated forms. It may be that these irregular, large, agglomerated forms are constituted of a mass of fine particles bound together on a globule of sulfuric acid carried over from the sulphonation process.

SUMMARY OF THE INVENTION

The present invention resides primarily in the discovery that water wet relatively pure styphnic acid may be reacted directly with a lead compound such as lead oxide, lead hydroxide, basic lead carbonate, or lead carbonate to form lead styphnate in situ in the wet mixture and that this wet product may be combined directly with the other normal ingredients of a priming mixture which may then be wet charged into primer cups without ever separating out or handling the lead styphnate in any dangerous or electrostatically sensitive conditions.

Although, as noted, in the practice of the preferred method the lead styphnate is not ordinarily separated out or handled by itself the reaction has been carried out without incorporating any of the other ingredients of a usual priming mixture so that the only end product was the new form of lead styphnate. Also, the reaction has been carried out with water solutions of the reactants and the end product carefully precipitated out, filtered, washed, and dried. Power diffraction tracings were obtained by X-Ray analysis of both of these materials and compared to similar tracings from other known forms of lead styphnate.

Analysis of these results confirms that the crystalline structure of the new form of lead styphnate differs from that of all other investigated compounds and that it has no equivalent in the "Powder Diffraction File" maintained by the Joint Committee on Powder Diffraction Standards. Further analysis establishes that its crystalline structure can be defined in a first approximation by a tetragonal unit cell structure having five lead styphnate molecules per unit cell.

The chief advantages of this in situ method of manufacturing priming mixtures are:

1. Substantial cost reduction through the elimination of the separate manufacture of lead styphnate;

2. Greatly increased safety through the elimination of the necessity to handle pure lead styphnate as a separate ingredient;

3. Reduction of environmental pollution potential through the elimination of certain production wastes which were inherent in the prior art processes for the production of lead styphnate;

4. Improved percussion sensitivity of the resulting mixtures;

5. Improved safety in handling wet priming mixture because of insensitivity of the mixture to initiation by shock, flame, static, etc.

BRIEF DESCRIPTION OF THE DRAWING

The single FIGURE of the drawing is a schematic representation of the tetragonal unit cell representing the new form of lead styphnate.

DESCRIPTION OF THE PREFERRED PROCESSES

As indicated, the key feature of this invention is the direct reaction between water wet relatively pure styphnic acid crystals and a lead compound such as lead oxide or lead hydroxide. As indicated, it is desirable that the styphnic acid be a relatively pure form and at least free from such impurities as sulfuric acid, the nitro derivatives of resorufin, the nitro derivatives of indophenol and/or the nitro derivatives of resazurin. If styphnic acid used in the preferred process contains such impurities, there is no opportunity to eliminate any undesirable products of a reaction with the impurity so that the undesirable products remain in the lead styphnate produced in situ and may cause stickiness and premature hardening of the mixture.

Although it is desirable that the reaction product be incorporated directly into a conventional priming mixture, it is important that, at the time the reaction referred to above takes place, certain of the other usual ingredients of a priming mixture should not be present in the reacting mass unless it can be established that such ingredients do not themselves react with one or the other of the reactants or with any intermediate compounds which may be formed. Thus, it has been established that gum arabic in water solution which is usually employed as a binder in wet priming mixtures, may be present while the reaction is going on, does not enter into that reaction, and may be desirable through its contribution to the mixability of the mixture and its effect in minimizing any tendency of the mixture to dry prematurely. The addition of a wetting agent also improves the mixing characteristics. Similarly, tetracene (1-Guanyl-4-nitrosoaminoguanyltetrazene) a commonly used sensitizer in ammunition priming mixtures, may be present during the reaction, does not enter into that reaction and is helpful in that the water content which is essential for the safe handling of tetracene contributes to maintaining the necessary moist environment for the reaction to proceed.

The other usual constituents of a priming mixture such as oxygen donors, fuels, and frictionators are preferably incorporated into the wet mixture after the lead styphnate reaction has been completed and prior to charging the wet mixture into rim fire cartridges or primer cups. As is the usual practice with wet charged mixtures, drying takes place after charging has been completed and the explosives do not return to their normal sensitivity until after drying. Thus, at no stage in the processing is there any occasion to handle dangerously sensitive explosives in bulk or to manipulate them when they are in a dry or otherwise dangerously sensitive condition.

A preferred method of preparing a rim fire priming composition in which the principal explosive ingredient is lead styphnate is as follows:

EXAMPLE I 3 lbs., 13 oz. (1,729 grams) of styphnic acid (wet weight with 20% water) is added to 3 oz. (85 grams) of gum arabic solution of a concentration of 4 lbs., 6 oz. (1,871 grams) gum arabic in 8 lbs., 13 oz. (4,000 grams) water and 12 oz. (340 grams) of tetracene (wet weight with 33% water) in the kettle of an industrial type Hobart mixer.

These ingredients are premixed for 1 minute in the Hobart mixer at room temperature of about 72° F.

To this premix there is added 1 lb., 12 oz. (794 grams) of lead hydroxide (wet weight with 15% water) and these ingredients are mixed in the Hobart mixer for about 4 minutes. As the ingredients react the temperature may rise to about 102° F.

An additional quantity of 1 lb., 12 oz. (794 grams) of lead hydroxide (wet weight with 15% water) is added and mixing continued in the Hobart mixer for an additional 4 minute period during which the temperature may rise to abouot 116° F. At this point, the reaction producing lead styphnate has been completed and the explosive ingredients of lead styphnate and tetracene are intimately mixed in a moist plastic mass with the gum arabic binder. Completion of the reaction may be verified by inspection of a sample at this point. This mixture does not require washing, filtering, or drying and except for the excess water which keeps it wet and insensitive, there is no waste product to be disposed of. It is preferable that the lead hdyroxide be added in two steps as above, both by reason of the completeness of the reaction and the type of lead styphnate resulting, as will be more fully discussed below.

As an aid to visual inspection of primed rim fire shells, it is now preferable to add about one scoop (½ oz. or 14 grams) of an inert dye such as Prussian blue which is thoroughly blended by mixing for 4 minutes in the Hobart mixer. The resulting green-colored mixture contrasts sharply with the brass interior of a rim fire case and is much more apparent on visual inspection than the yellowish color characteristic of the lead styphnate and tetracene mixtures. In the event that other inspection systems which do not depend on a visual image are used, this step may be eliminated. During this mixing cycle the mixture can be expected to cool to about 106° F.

At this point, the remaining ingredients of a rim fire priming mixture may be formed into a premix of the oxygen donor, barium nitrate, and the frictionator, ground glass. 2 lbs., 2 oz. (963 grams) of barium nitrate (dry weight) and 4 lbs., 2 oz. (1,869 grams) of ground glass (dry weight) are separately premixed and then blended with the explosive ingredients during two successive 2 minute mixing cycles in the Hobart mixer.

In further work it has been noted that mixing has been facilitated by the incorporation of a small amount of a wetting agent, Triton, in the water with which the starting materials have been wetted.

The yield is about 14½ lbs. (6,590 grams) of moist plastic rim fire priming mixture which is insensitive to shock, friction, and static electricity and which cannot even be detonated by the explosion of a blasting cap buried in the plastic mixture. As a result the mixture can be safely handled and can be extruded through metering devices or rubbed into the measuring apertures of the conventional charging plates without fear of accidental explosion.

Obviously, the mixture should be kept wet and plastic until used and the usual precautions should be observed to avoid the possibility that any of the mixture dries on or in charging equipment, storage receptacles and the like. Any mixture which is allowed to become dry or which hardens to such a degree as to become unworkable should be handled and disposed of with all of the precautions appropriate to sensitive primary explosives. The mixture is dried after charging into rim fire shells and thereafter exhibits normal percussion sensitivity and igniting power.

A similar procedure using lead oxide (litharge) as one of the reactants is set forth below in the production of an equivalent rim fire priming mixture.

EXAMPLE II 3 lbs., 13 oz. (1,729 grams) of styphnic acid (wet weight with 20% water) is added to 7 oz. (198 grams) of water and 3 oz. (85 grams) of gum arabic solution, of a concentration of 4 lbs., 6 oz. (1,871 grams) gum arabic in 8 lbs., 13 oz. (4,000 grams) of water and 12 oz. (340 grams) of tetracene (wet weight with 33-⅓% water) and two scoops of Prussian blue dye (as an inspection aid) in the kettle of an industrial type Hobart mixer.

These ingredients are premixed for 1 minute in the Hobart mixer at room temperature of about 72° F.

A hollow is formed in the center of the mass of moist premix by working with the hands or with a rubber spatula and in this hollow there is added 1 lb., 7 oz. (652 grams) of litharge, PbO (dry weight) and these ingredients are mixed in the Hobart mixer for about 3 minutes. As the ingredients react, the temperature may rise to about 114° F.

Another hollow is formed in the center of the mass of the partially reacted mix and an additional quantity of 1 lb., 7 oz. (652 grams) of litharge (dry weight) is added in this hollow and mixing continued in the Hobart mixer for a period of about 4 minutes during which the temperature may rise to about 124° F. Mixing may be continued for an additional period of 4 minutes during which the temperature may be expected to drop to about 106° F.

At this point the remaining ingredients of a rim fire priming mixture may be added such as the oxygen donor, barium ntirate and a frictionator, ground glass. 2 lbs., 2 oz. (963 grams) dry weight of barium nitrate and 4 lbs., 2 oz. (1,869 grams) dry weight of ground glass are separately premixed and then blended with the moist explosive ingredients produced above during two successive 2 minute mixing cycles with the Hobart mixer.

As noted in Example I, it has been found desirable to incorporate a wetting agent with the water used in wetting the starting materials.

The yield is about 14 ⅓ lbs. (6,500 grams) of moist, plastic, rim fire priming mixture which is in all respects equivalent to that produced in Example I and which is charged, dried, and used in the same way.

EXAMPLE III

A shotshell and center fire priming mixture may be produced by the following procedure:

278 grams of styphnic acid (wet with 20% water) are added to 10 cc's of gum arabic solution (2,090 grams gum arabic in 4,000 cc's water) and 60 grams of tetracene (wet with 33% water) in the kettle of an industrial type Hobart mixer.

These ingredients are premixed in the Hobart mixer for 1 minute at room temperature which in this instance was 79°F.

To this premix there is added 129 grams of lead hydroxide (wet with 15% water) and these ingredients are mixed in the Hobart mixer for about 4 minutes. As the ingredients react the temperature may rise to about 95° F.

An additional quantity of 129 grams of lead hydroxide (wet with 15% water) is added and mixing continued for about another 4 minutes during which the temperature may rise to about 108° F.

As in Examples I and II it has been found desirable to incorporate a wetting agent.

To form a typical shotshell or center fire primer mix, it is necessary to add an oxygen donor and one or more fuels which tends to diminish the violence of the explosion by dilution and which by combination with the oxygen donor tend to improve the heat output and powder igniting efficiency of the mixture.

One suitable fuel is calcium silicide (Ca $Si_2$) and 55 grams of that material (dry weight) may be combined with the moist explosive ingredients in a 4 minute mixing cycle in the Hobart mixer during which the temperature will be lowered to about 92° F.

Another suitable fuel is antimony sulfide ($Sb_2S_3$) and 70 grams of this fuel (dry weight) is combined with 415 grams of barium nitrate (dry eight). These materials are premixed with each other and then mixed into the explosive mixture produced above by tw successive 2 minute mixing cycles in the Hobart mixer.

The yield is about 1,145 grams of moist, plastic, shotshell or center fire priming mixture which in the moist state is insensitive to shock, friction or static electricity and which can be wet charged into primer cups in the traditional way and may be provided with the usual anvil or anvil and battery cup.

EXAMPLE IV

A shotshell and center fire priming mixture may also be produced by the following procedure:

Calcium silicide which is used as a fuel in primers does not enter into the reaction producing lead styphnate and may, if desired, by incorporated in the initial portion of the process. In this example 11 oz. (312 grams) of calcium silicide (dry weight), 7 oz. (198 cc's) of water, 1 oz. (28 grams) of gum solution of a concentration similar to that described above in Examples I and II, 3 lbs., 7.6 oz. (1,575 grams) of styphnic acid (wet with 20% water) and 12 oz. (340 grams) of tetracene (wet with 33⅓% water) are combined in the kettle of an industrial type Hobart mixer and premixed for about 1 minute at room temperature.

A hollow is formed in the center of this moist mass of premix and in this hollow there is added 1 lb., 4.6 oz. (584 grams) dry weight of litharge and these ingredients are mixed for about 3 minutes in the Hobart mixer. As the ingredients react the temperature may rise to about 106° F.

Another hollow is formed in the center of the mass of partially reacted material and an additional quantity of 1 lb., 4.6 oz. (584 grams) (dry weight) of litharge is added in this hollow and mixing continued in the Hobart mixer for about 4 minutes. The temperature may rise to about 115° F. and the reaction should be complete. Mixing may be continued for about another 4 minutes and the temperature should fall to about 98° F.

The remaining ingredients of a shotshell priming mixture are more fuel and an oxygen donor. To complete the mixture 14 oz. (397 grams) of antimony sulfide (dry weight) are separately premixed and then blended with the moist explosive ingredients in two successive 2 minute cycles in the Hobart mixer.

The yield is about 14 1/5 lbs. (6,440 grams) of moist, plastic, shotshell priming mixture conforming substantially to that produced under Example III and usable interchangeably therewith.

As in the previous examples, the incorporation of a wetting agent is desirable.

EXAMPLE V

Sample for X-Ray Diffraction Study 267 grams of styphnic acid (wet with 20% water) was combined with 35 cc's of additional water, 5 cc's of a solution of Triton 100X wetting agent (140 grams of Triton in 4 liters water) and 145 grams of lead hydroxide (wet with 16% water) and cycled for 4 minutes in a Hobart mixer.

To this mixture there was added another 145 grams of lead hydroxide (wet with 16% water) and the mass was cycled for 6 minutes in a Hobart mixer and then recycled for another 3 minutes in the Hobart mixer.

The end product is the new form of lead styphnate in the form of small yellowish agglomerated particles without definite crystalline form under visual examination. It is a primary explosive.

The sample was labelled and set aside for X-Ray diffraction study.

EXAMPLE VI

Sample for X-Ray Diffraction Study 278 grams of styphnic acid (wet with 20% water) was combined with 50 cc's of additional water and 5 cc's of the wetting agent solution referred to in Example V and 103 grams of dry lead oxide.

These reactants were cycled for 4 minutes in a Hobart mixer.

An additional 103 grams of dry lead oxide was then added and cycled for 6 minutes in a Hobart mixer and then recycled for an additional 3 minutes.

The end product is the new form of lead styphnate in the form of small yellowish agglomerated particles without definite crystalline form under visual examination. It is a primary explosive.

The sample was labelled and set aside for X-Ray diffraction study.

EXAMPLE VII

Sample for X-Ray Diffraction Study 305 grams of styphnic acid (wet with 20% water) was combined with 60 cc's of additional water and 5 cc's of the wetting agent solution referred to in Example V and 179 grams of dry basic lead carbonate.

These reactants were cycled for 4 minutes in a Hobart mixer.

An additional 179 grams of dry basic lead carbonate was then added and cycled for 6 minutes in a Hobart mixer and then recycled for an additional 6 minutes.

The end product is the new form of lead styphnate in the form of small yellowish agglomerated particles without definite crystalline form under visual examination. It is a primary explosive.

The sample was labelled and set aside for X-Ray diffraction study.

EXAMPLE VIII

Sample for X-Ray Diffraction Study 278 grams of styphnic acid (wet with 20% water) was combined with 80 cc's of additional water and 5 cc's of the wetting agent solution referred to in Example V and 124 grams of dry normal lead carbonate.

These reactants were cycled for 4 minutes in a Hobart mixer.

An additional 124 grams of dry, normal lead carbonate was then added and cycled for 6 minutes in a Hobart mixer and then recycled for an additional 25 minutes.

The end product is the new form of lead styphnate in the form of small yellowish agglomerated particles without definite crystalline form when subjected to visual examination. It is a primary explosive.

The sample was labelled and set aside for X-Ray diffraction study.

EXAMPLE IX

Sample for X-Ray Diffraction Study

In order to isolate the new form of lead styphnate in the form of discrete crystals the following procedure was followed:

26.7 grams of styphnic acid (wet with 20% water) was suspended in 250 cc's of water at 80° F.

To this, with stirring, was added 13.0 grams of lead hydroxide (wet with 16% water) and stirring continued for 5 minutes.

13.0 grams of lead hydroxide (wet with 16% water) was then added and the stirring was continued for 10 minutes.

The precipitate was removed from the reaction vessel, filtered, washed and dried.

The product was a primary explosive in the form of brown rectangular parallelopipeds.

The sample was labelled and set aside for X-Ray diffraction study.

EXAMPLE X

Sample for X-Ray Diffraction Study 26.7 grams of styphnic acid (wet with 20% water) was suspended in 250 cc's of water at 75° F. To this, with stirring, was added 11.0 grams of lead hydroxide (wet with 16% water) and stirring was continued for 10 minutes.

The precipitate was removed from the reaction vessel, filtered, washed and dried.

The product was in the form of yellowish parallelopipeds or relatively thick plates and was not a primary explosive. It is believed to be an intermediate product which is formed during the first mixing step of the preferred process of forming the new form of lead styphnate. For convenience, we have identified it with the name lead acid styphnate.

With the proper proportions of ingredients and with the maintenance of the proper conditions as set forth in the examples above, it appears that the reaction between the styphnic acid and the lead compound always goes to completion with substantially no unreacted material remaining in the mass and with no by-products of the reaction except for gases which may be released or for water which remains as water of hydration in the lead styphnate crystals or as free water which is eliminated during the normal drying of the priming mixture.

The reaction with litharge appears to be represented by the following equation:

$$PbO + (NO_2)_3C_6H(OH)_2 \rightarrow C_6H(NO_2)_3O_2Pb \cdot H_2O$$

The reaction with lead hydroxide appears to be represented by the following equation:

$$Pb_2O(OH)_2 + 2(NO_2)_3C_6H(OH)_2 \rightarrow 2C_6H(NO_2)_3O_2Pb \cdot H_2O + 2H_2O$$

(Note that there is not a universal agreement that the above formula is correct for lead hydroxide, some authorities preferring to write it as $Pb(OH)_2$.)

The reaction with basic lead carbonate appears to be represented by the following equation:

$$2PbCO_3 \cdot Pb(OH)_2 + 3(NO_2)_3C_6H(OH) \rightarrow$$

$$3(NO_2)_3C_6H\,O_2Pb \cdot H_2O + 2CO_2 + H_2O$$

The reaction with normal lead carbonate appears to be represented by the following equation:

$$PbCO_3 + (NO_2)_3 C_6H(OH)_2 \rightarrow$$

$$(NO_2)_3C_6HO_2Pb \cdot H_2O + CO_2 \uparrow + H_2O$$

Thus, in the commercial production of primers there is no necessity for the usual processes of filtering, washing, and drying which separate out and require special handling of dangerously sensitive material.

As noted above, gum arabic, tetracene, blue dye and some fuels such as calcium silicide do not enter into the reaction or interfere with the completion of the reaction and may be incorporated with the styphnic acid prior to the reaction. Indeed, to the extend that such ingredients add water to the mixture, they contribute to maintaining the moisture content which is necessary for the reaction to proceed and for safety reasons. Other ingredients, and praticularly an oxygen donor such as lead nitrate or barium nitrate, should definitely not be added to the mixture until the reaction producing lead styphnate has been completed.

It may be noted that I prefer to use barium nitrate as the oxygen donor on the basis that its use tends to minimize the amount of lead discharged into the air as the result of handling or the explosion of the reactants or the final priming charge. Although the mixtures using barium nitrate tend to be less percussion sensitive than mixtures using lead nitrate, the lead styphnate produced by my new process is more precussion sensitive than the prior art lead styphnate so that there is a net gain in percussion sensitivity of mixtures made by using my new process.

It has been noted above that I prefer to add the lead compound in two steps. My earlier work on this process demonstrated that a more powerful and more percussion sensitive lead styphnate resulted when this procedure was followed. I believe that this effect is the result of a more complete reaction and that it results in the formation of a somewhat different crystalline form of lead styphnate. Thus, I prefer to add one half of the stoichiometric amount of lead oxide (or lead hydroxide, basic lead carbonate, or normal lead carbonate) to the styphnic acid in a first mixing cycle followed by the addition of the second half of the stoichiometric amount of lead oxide (or lead hydroxide, basic lead carbonate, or lead carbonate) rather than to add the entire stoichiometric amount of lead oxide (or lead hydroxide, basic lead carbonate, or lead carbonate) to the styphnic acid in a single mixing cycle.

When the intermediate product resulting from the first stage of the reaction involving the use of only half of the preferred stoichiometric amount of the lead salt is precipitated out, filtered, washed, and dried it is found to be entirely different material which for convenience has been labelled as Lead-Acid-Styphnate and which is not a primary explosive.

In a recent study of typical rim fire priming mixtures corresponding generally to Examples I and II, identical quantities of identical materials were reacted first in the two step mixing cycle and secondly in a single step mixing cycle. When the resulting priming mixtures were charged in identical quantities and in the same manner in 22 Long Rifle rim fire cartridge cases and tested for drop test sensitivity to percussion, the product of the two step cycle had a sensitivity of $\overline{X}$ 4.14 inches and $\acute{o}$ 1.35 inches while the product of the single step mixing cycle had a sensitivity of $\overline{X}$ 5.38 inches and $\acute{o}$ 1.68 inches.

It appears probable that when made in the single step mixing cycle, even though the full amount of the lead salt is used, the resulting lead styphnate is a mixture of the lead acid styphnate and the desired product to which this invention relates.

The following test results show the performance of priming mix made according to present invention as compared to a present commercial mixture using the form of lead styphnate produced in accordance with U.S. Pat. No. 1,999,728.

22 Cal. Rim Fire Shells

Drop Test 2 oz. Ball — 50 per Height

|  | Commercial (lead nitrate oxidizer) | Using New Form of Lead Styphnate (barium nitrate oxidizer) |
|---|---|---|
| $\overline{X}$ | 5.36" | 4.72" |
| $\acute{o}$ | 1.42" | 1.12" |

22 Cal. Standard Velocity Cartridges

| | | |
|---|---|---|
| Velocity | 1,087 fps | 1,076 fps |
| Pressure | 15,600 psi | 15,700 psi |

Shotshell Shooting Test

12 Ga. H. Magnum No. 1 Buck

| | | Std. | Experimental |
|---|---|---|---|
| Normal | Velocity | 1,142 fps | 1,142 fps |
| | Pressure | 10,900 psi | 11,000 psi |
| −20°F | Velocity | 826 fps | 830 fps |
| | Pressure | 7,800 psi | 8,000 psi |
| +150°F | Velocity | 1,185 fps | 1,170 fps |
| | Pressure | 12,400 psi | 12,300 psi |

Characterization of the New Form of Lead Styphnate

In the characterization of the new form of lead styphnate, the samples described in Examples V through IX were prepared as well as the intermediate product to which Example X is direct.

In all cases except that of Example X, the end product is a primary explosive conforming in elemental chemical analysis to normal lead styphnate $C_6H(NO_2)_3O_2Pb\cdot H_2O$ and characterized by an extremely low order of sensitivity to shock, friction, or electrostatic discharge when wet with as little as 10% water which is about half the water content resulting from the practice of the preferred process of producing the pure explosive as in Examples V through IX. The samples produced in accordance with Examples V, VI, VII, and VIII were in the form of small yellowish agglomerated particles without definite crystal form under visual examination and the sample produced in accordance with Example IX was brown in color and in the form of well defined crystals of rectangular parallelopiped form.

Explosion Point

The explosion point is too high to be accurately measured on the usual pure copper temperature gradient bar but when measured in a copper block containing a thermometer well it appears that either the agglomerates or the crystalline form of Example VIII explode at about 297° C.

Electrostatic Sensitivity

When tested for electrostatic sensitivity, the crystalline form of the new lead styphnate produced in accordance with Example IX was found to fire as follows:
Dry 6 fires in 10 tries with discharge of 300 mmfd. capacitor charged 100 volts.
Dry 10 fires in 10 tries with discharge of 300 mmfd. capacitor charged to 200 volts.
15% water 2 fires in 10 tries with discharge of 300 mmfd.
capacitor charged to 300 volts.
15% water 5 fires in 10 tries with discharge of 300 mmfd.
capacitor charged to 500 volts.
15% water 5 fires in 10 tries with discharge of 300 mmfd.
capacitor charged to 1000 volts.
20% water 0 fires in 10 tries with discharge of 300 mmfd.
capacitor charged to 1000 volts.

A sample produced in accordance with Example V was found to fire as follows:
Dry 4 fires in 10 tries with discharge of 300 mmfd. capacitor charged to 100 volts.
Dry 8 fires in 10 tries with discharge of 300 mmfd. capacitor charged to 200 volts.
10% water 0 fires in 10 tries with discharge of 300 mmfd.
capacitor charged to 1000 volts.

For comparison, a sample of normal lead styphnate prepared in the factory of applicant's assignee in accordance with the procedure outlined in U.S. Pat. No. 1,999,728 was similarly tested and found to fire as follows:
Dry 10 fires in 10 tries with discharge of 300 mmfd. capacitor charged to 100 volts.
15% water 10 fires in 10 tries with discharge of 300 mmfd.
capacitor charged to 100 volts.
20% water 9 fires in 10 tries with discharge of 300 mmfd.
capacitor charged to 100 volts.

The significance of the above tests is realized by remembering that the sample produced in accordance with U.S. Pat. No. 1,999,728 is representative of that now widely used in Industry and is identical with the material which has been produced and loaded in the factory of applicant's assignee since about 1930. The sample produced in accordance with Example V is representative of that which is produced in situ in the preferred processes of primer manufacture in accordance with Examples I through IV. As produced and handled for charging in accordance with Example I through IV, the mixture is at the 10% water content and none of the explosive samples fire when subjected to the 1000 volt discharge. This must be contrasted with the explosive produced in accordance with U.S.

Pat. No. 1,999,728 where 9 out of 10 samples fire when subjected to a 100 volt discharge.

Sensitivity to Explosions

By comparison, a sample of a mixture of the new form of lead styphnate and the sensitizer tetracene, as produced with 21.5% water, will not detonate even though a No. 6 blasting cap is buried in a mass of the explosive and exploded while a charge of the explosive produced in accordance with U.S. Pat. No. 1,999,728 and with about 20% water will explode with high order detonation when a blasting cap is exploded in a mass of the explosives.

Percussion Sensitivity

In sharp contrast to its relative insensitivity in the wet form, the new explosive and mixtures containing it show, in the dry form in which they are ultimately used, a higher degree of percussion sensitivity than mixtures based on the prior forms of lead styphnate.

X-Ray Diffraction

1. Background

Determination of crystalline solids by their crystal structure is the most thorough and unambiguous characterization, since it presents the coordinates $x_i$, $y_i$, $z_i$ of each atom of the material. This characterization, however, requires considerable effort and expense, particularly for complicated compounds. Single crystals are a must for a complete structure analysis, a condition that cannot always be met. But less demanding characterization by X-Ray diffraction is often sufficient to establish the identity of crystalline material and to set it apart from other, similar materials. The crystal structure need not be known for this identification, nor are single crystals required. The diffraction patterns obtained from the polycrystalline powder or conglomerate with a monochromatic x-radiation suffice. These patterns, recorded on film or with a goniometer, measure Bragg angles $\theta$ and approximate intensities I of the reflections. According to Bragg's equation $$n \lambda = 2d \sin \theta$$

or better for our consideration $$d = \frac{n\lambda}{2 \sin \theta}$$

each reflection angle $\theta$ measured in a goniometer represents a lattice spacing $d$, when recorded with the monochromatic X-Ray wavelength $\lambda$. By dealing with lattice spacings d instead of the Bragg angles $\theta$, one eliminates the wavelength $\lambda$ used in the determination of d and has therefore a basis for unambiguous comparison.

The atoms (ions, molecules) in any crystalline material are arranged in a three-dimensional, regular, periodic lattice, which can be thought of as representing various "planes". Reflection of an X-Ray wave can occur on any of these planes, if the conditions described above are met and the partial waves scattered from the lattice points superpose to a measurable intensity. There is an infinite number of possible planes in a three-dimensional lattice, but only those meeting the above conditions are observed.

The crystalline structure of a solid is described (without detail) by its "unit cell", the smallest possible crystal. In the crystals of lowest symmetry, i.e., triclinic, the unit cell is defined by the lengths of the three vectors $a$, $b$, $c$, and the three angles $\alpha$, $\beta$, $\lambda$. In the crystals of highest symmetry, i.e., of the cubic system, this reduces to one Vector, a. The distance d between consecutive planes in one set characterized by its "Miller Indices", $h$, $k$, $l$, is calculated by a general formula that is very complicated for the triclinic systems, becomes gradually simpler for systems of higher symmetry, and is reduced in the cubic system to $$\frac{1}{d} = \sqrt{\frac{h^2 + k^2 + l^2}{a}}$$

Without going into detail that would exceed the scope of this specification, it suffices to say that the "Miller Indices" are related to the sections cut off by a plane from the axes of the crystal coordinate system.

Samples of the explosives produced in accordance with Examples V, VI, VII, VIII, and IX and of the explosives produced in accordance with U.S. Pat. Nos. 1,999,728 and 2,589,703 have been made and subjected to X-Ray diffraction analysis of powder samples. The tracings therefrom, record Bragg angles $\theta$ and approximate intensities of the reflections. Similar X-Ray diffraction tracings were obtained from samples of the materials of production, i.e., styphnic acid, lead nitrate and lead hydroxide and for the intermediate product of Example X which we have called lead acid styphnate to eliminate the possibility that remnants of the raw materials of the intermediate product remained to confuse or contribute to the reflections recorded.

For comparison, the Bragg angles $\theta$ have been converted to d-values as described above and d-values and intensity ratios for the strongest lines are tabulated below. This comparison confirms that the explosives produced in accordance with Examples V, VI, VII, VIII, and IX are in fact the same material and are not contaminated with remnants of the raw materials or of the intermediate materials. For example:

| New Form of Lead Styphnate Examples V, VI, VII, VIII, and IX | | Lead Styphnate U.S. Pat. No. 1,999,728 | | "Cubic" Lead Styphnate U.S. Pat. No. 2,589,703 | | Lead Acid Styphnate Example X | | Styphnic Acid | |
|---|---|---|---|---|---|---|---|---|---|
| d(A) | I/Io* ×100 | d(A) | I/Io* ×100 | d(A) | I/Io* ×100 | d(A) | I/Io* ×100 | d(A) | I/Io* ×100 |
| 7.96 | 55 | 7.75 | 100 | 8.56 | 30 | 12.18 | 75 | 6.28 | 40 |
| 7.16 | 45 | 5.68 | 37 | 7.79 | 75 | 6.43 | 22 | 3.70 | 100 |
| 5.33 | 50 | 4.33 | 70 | 4.62 | 24 | 5.86 | 27 | 2.61 | 60 |
| 3.98 | 35 | 3.70 | 57 | 3.99 | 38 | 4.84 | 20 | | |
| 3.59 | 100 | 3.19 | 80 | 3.89 | 61 | 4.10 | 100 | | |
| 3.27 | 55 | 3.03 | 46 | 3.19 | 100 | 3.65 | 45 | | |
| 3.18 | 55 | 2.94 | 38 | 2.94 | 62 | 3.52 | 24 | | |
| 2.92 | 30 | 2.55 | 30 | | | 3.46 | 63 | | |
| 2.61 | 30 | | | | | 3.12 | 52 | | |
| | | | | | | 3.07 | 57 | | |
| | | | | | | 2.85 | 80 | | |

*Io intensity of strongest reflection

Powder Diffraction File

It has long been recognized by crystallographers that anyone who records the distance d for a sufficiently large number of planes in a crystal characterizes that crystal even without knowing its unit cell or the positions of the atoms within the unit cell. This characterization becomes even more reliable by recording the intensity with which these planes reflect X-radiation. In recognition of this superb characterization capability, an international body, the "Joint Committee on Powder Diffraction Standards", 1601 Park Lane, Swarthmore, Pennsylvania 19801, has been formed and on punched cards and in computer memory banks has filed the d-values and corresponding intensities for many thousands of materials to make them available as a source of identification. The number of compounds so recorded grows yearly and provides a valuable supplement to other sources of identification. Including the most recent supplements, the File now includes the following materials related to the new form of lead styphnate to which this patent application relates. The marginal number relate to the card in the File on which the data is recorded.

| File No. | |
|---|---|
| 11-825 | Styphnic Acid (2,4,6-Trinitroresorcinol) |
| 9-769 | Lead Styphnate $C_6H_3N_3O_8Pb$ |
| 23-1757 | Lead — 2,4,6-Trinitroresorcinate Hydrate $C_6HN_3O_8Pb.H_2O$ |
| 23-1756 | Lead Hydroxide — 2,4,5-Trinitroresorcinate $C_{12}H_8N_6O_{23}Pb_5$ |
| 23-1754 | Lead Hydroxide — 2,4,6-Trinitroresorcinol $C_{18}H_{10}N_6O_{31}Pb_{13}$ |
| 23-1753 | Lead Hydroxide — 2,4,6-Trinitroresorcinate $C_6H_3N_3O_{10}Pb_2$ |

The multiplicity of compounds comes from the fact that styphnic acid is a complicated molecule with two acidic hydrogen atoms and many steric possibilities to combine with lead. These complicated molecules can be arranged quite differently in a crystal. There probably exist more compounds which have not been recorded. The question of purity arises: identification by d-values is unambiguous only if a substance is not adulterated by other substances, impurities, isomers, etc.

The "Powder Diffraction File" contains information about all the above compounds by d-values and relative intensities I/Io (Io=strongest line). Styphnic acid and lead styphnate are also characterized by their simple crystal data:

Styphnic acid: hexagonal
 a = 12.7A   c = 10.0A
Lead styphnate: monoclinic
 a = 10.06A   b = 12.58A   c = 8.05A
 β = 91.9°

A comparison of the d-values listed in the "File" was made against those tabulated above from X-ray tracings made from the following materials:

| Lead Styphnate | U.S. Pat. No. 1,999,728 |
|---|---|
| "Cubic" lead styphnate | U.S. Pat. No. 2,589,703 |
| Lead acid styphnate | Example X |
| New Form of lead styphnate | Examples V, VI, VII, VIII, and IX |

No close match was observed. Also, the d-values of the strongest lines of the raw materials of production, i.e., styphnic acid, lead nitrate, and lead hydroxide were compared and the possibility was eliminated that some remnants of the raw materials contributed to the numerous reflections.

The table is restricted to the strongest reflections for reasons of clarity; to list all of the very numerous lines would only confuse the issue. It can be said with certainty that the new form of lead styphnate is different from any of those tabulated above and is not identical with any of those described in the "File".

Four diagrams of the new form of lead styphnate were obtained as follows:

| New Form of Lead Styphnate | Agglomerated (Example V) |
|---|---|
| New Form of Lead Styphnate | Crystalline (Example IX) |
| New Form of Lead Styphnate | Made from styphnic acid + lead oxide Agglomerated (Example VI) |
| New Form of Lead Styphnate | Made from styphnic acid + basic lead carbonate Agglomerated (Example VII) |

Under visual examination the tracings were virtually identical and when d-values were calculated there was close agreement thus providing assurance that the new form of lead styphnate is consistently produced in spite of different production procedures. Only visual examination was made of the tracing from the Explosive of Example VIII (made from styphnic acid and normal lead carbonate) but this also confirmed that the X-Ray diffraction pattern was virtually identical to that produced by the other procedures outlined in Examples V through IX.

The X-Ray diffraction diagram of the new form of lead styphnate is different from all others in the table above or in the "Powder Diffraction File". It excels by simplicity, with only a few strong lines. This simplicity invites an attempt to go beyond a mere recording of d-values for identification and to try to index the d-values of the Bragg equation $$n = 2d \sin \theta$$

by the corresponding Miller indices of the equation $$\frac{1}{d} = \sqrt{\frac{h^2 + k^2 + l^2}{a}}$$

No cubic indexing was found by the procedure described. But an attempt with the procedure for the tetragonal system, which is more complicated and will not be described here for reasons of brevity, resulted in a satisfactory description of the structure by a tetragonal unit cell of the dimensions $$a = 11.22A$$

$$c = 7.19A$$

Table II

Description of the New Form of Lead Styphnate by Tetragonal Structure

| $\theta°$ (measured) | I/Io (approx.) | d(A) | Miller Indices h, k, l | d(A) calculated* |
|---|---|---|---|---|
| 5.55 | 55 | 7.96 | 110 | 7.95 |
| 6.18 | 45 | 7.16 | 001 | 7.19 |
| 7.83 | 10 | 5.65 | 020 | 5.62 |
| 8.30 | 50 | 5.33 | 111 | 5.33 |
| 8.90 | 20 | 4.98 | 120 | 5.02 |
| 11.15 | 35 | 3.98 | 220 | 3.97 |
| 12.40 | 100 | 3.59 | 002 | 3.59 |
| 13.60 | 55 | 3.27 | 112 | 3.27 |
| 14.00 | 55 | 3.18 | 131 | 3.18 |
| 15.28 | 30 | 2.92 | 122 | 2.92 |
| 17.15 | 30 | 2.61 | 041 | 2.61 | a = 11.22A, c = 7.19A

*by formula:

$$d = \frac{a}{\sqrt{h^2 + k^2 + l^2 \left(\frac{a}{c}\right)^2}}$$

Figure 1:
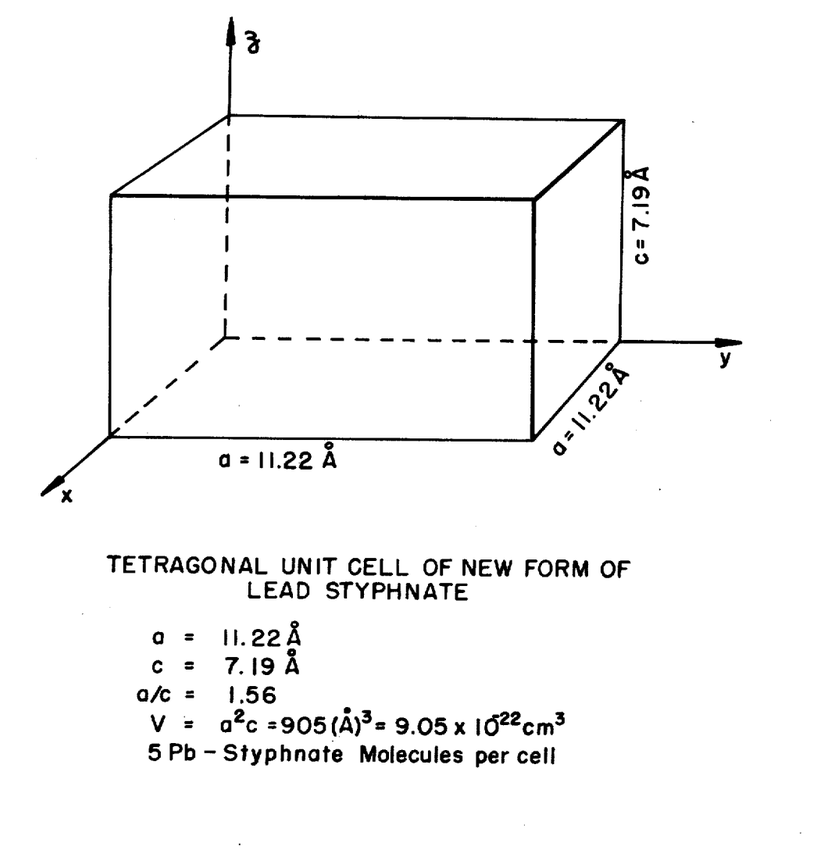

Table II contains the measured Bragg angles, Miller indices, h, k, l, and Bragg angles calculated from this structure. The agreement is very good. The figure shows the unit cell and its dimensions.

The volume $a^2b$ of a unit cell is $905A^3 = 9.05 \times 10^{-22} cm$ and there are, therefore, $1.10 \times 10^{21}$ unit cells per cm$^3$. Since the density (grams/cm$^3$) is 4.3, one unit cell represents a mass of $3.89 \times 10^{-21}$ g. The molecular weight of the lead styphnate is 468.19. This means that:

$6.02 \times 10^{23}$ molecules have a mass of 468.19 g
1 molecule has a mass of $7.77 \times 10^{-22}$ g
1 unit cell of $3.89 \times 10^{-21}$ g contains therefore
$\frac{3.89 \times 10^{-21}}{7.77 \times 10^{-22}} = 5.00$ molecules It needs to be emphasized that the description of a crystallographic structure composed of such complicated molecules by this simple tetragonal cell is only a coarse approximation. But it is safe to say that the molecules, each of which contains 22 atoms, are arranged in such a way that a cell of the form seen in the figure, containing 5 molecules, can approximately represent its structure. In other words, one would arrive at a new form of lead styphnate crystallite by stacking up unit cells of the figure in three dimensions.

Reference may also be made to the form of lead styphnate produced in accordance with Brun U.S. Pat. No. 2,239,547. The inventor of that patent had many years of experience in the production and utilization of lead styphnate in accordance with U.S. Pat. No. 1,999,728 and the statement in U.S. Pat. No. 2,239,547 to the effect that "X-Ray photographs of the mixture show the distinctive pattern of normal lead styphnate" refer to the then standard commercial form of lead styphnate as produced in the plant of applicant's assignee in accordance with U.S. Pat. No. 1,999,728, until that process began to be displaced by the presently preferred process described in this application. The new form of lead styphnate to which this application relates, as confirmed from visual comparison of X-Ray diffraction tracings with the X-Ray diffraction tracings of lead styphnate produced in accordance with U.S. Pat. No. 2,239,547, is distinctively different and it is confirmed that the form of lead styphnate produced in accordance with U.S. Pat. No. 2,239,547 is substantially identical to that produced in accordance with U.S. Pat. No. 1,999,728.

Reference may also be made to the form of lead styphnate produced in accordance with Garfield U.S. Pat. No. 2,295,104, where a form of lead styphnate is produced by treating styphnic acid in suspension or solution with a solution of lead acetate or other weak organic acid. It should be noted that this reaction for producing lead styphnate would not be useful in accordance with applicant's method of producing the lead styphnate in situ in a primer mixture for, without opportunity for filtering, washing, and drying, the mixture would remain contaminated with acetic acid or the other weak organic acids resulting from the reaction with lead acetate, lead propionate, or lead lactate. As described in the patent, this form of normal lead styphnate appears to conform quite closely in crystal form and characteristics to the normal lead styphnate produced in accordance with the methods described in the literature or in U.S. Pat. No. 1,999,728. Further, recently produced samples, made in accordance with Example I of U.S. Pat. No. 2,295,104, have been subject to X-Ray diffraction study and it has been confirmed by visual examination of the tracings that the procedure described in this patent produces the classic form of normal lead styphnate as produced under U.S. Pat. No. 1,999,728 and is distinctively different from that produced in accordance with the methods disclosed herein.

From the crystallographic data, the following conclusions can be supported.

There is a large variety of crystalline structures of lead compounds of styphnic acid. This is understandable from the complicated form of the molecule and the existence of many isomers. The new form of lead styphnate has a structure distinctly different from that of all other substances considered in this study or described in the "Powder Diffraction File". It excels by its relative simplicity and can be described in first approximation by the unit cell of the single FIGURE of the drawing.

Having now described the invention, what is new and is desired to be secured by Letters Patent is:

1. The method of making a new form of normal lead styphnate which consists of reacting styphnic acid free from the impurities usually present in commercial styphnic acid in the presence of water with a non-explosive compound of lead selected from the group of lead compounds consisting of lead oxide, basic lead carbonate, lead carbonate, and lead hydroxide to produce a workable, granular, wet mass of the new form of normal lead styphnate and no by products of the reaction except water or water and carbon dioxide, said new form of normal lead styphnate in the wet state being insensitive to heat, shock, friction, or electrostatic discharge.

2. The method of claim 1, wherein the stoichiometric amount of the non-explosive lead compound is divided into at least two substantially equal parts and those equal parts are reacted in turn with the whole quantity of the styphnic acid in separate but successive mixing cycles.

3. The method of claim 1, wherein said styphnic acid is substantially free from sulphuric acid, the nitro derivatives of resorufin, the nitro derivatives of indophenol and the nitro derivatives of resazurin.

4. The method of claim 3, wherein the stoichiometric amount of the non-explosive lead compound is divided into at least two substantially equal parts and those equal parts are reacted in turn with the whole quantity of the styphnic acid in separate but successive mixing cycles.

5. A new form of normal lead styphnate characterized by crystalline lattice dimensions which produce Bragg diffractions with relative intensities substantially as tabulated herein:

| d(A) | I/Io |
|---|---|
| 7.96 | 55 |
| 7.16 | 45 |
| 5.33 | 50 |
| 3.98 | 35 |
| 3.59 | 100 |
| 3.27 | 55 |
| 3.18 | 55 |
| 2.92 | 30 |
| 2.61 | 30. |

6. A new form of normal lead styphnate characterized by a tetragonal unit cell structure of dimensions substantially as follows: $a = 11.22$A $a = 11.22$A $c = 7.19$A and having five lead styphnate molecules per unit cell.

* * * * *